US006635483B1

(12) United States Patent
Telerman et al.

(10) Patent No.: US 6,635,483 B1
(45) Date of Patent: Oct. 21, 2003

(54) COMPOUND AND METHODS OF INHIBITING OR STIMULATING PRESENILIN 1 AND RELATED PHARMACEUTICALS AND DIAGNOSTIC AGENTS

(75) Inventors: Adam Telerman, Paris (FR); Robert Amson, Paris (FR)

(73) Assignee: Societe Molecular Engines Laboratories, Paris (FR)

( * ) Notice: Subject to any disclaimer, the term of this patent is extended or adjusted under 35 U.S.C. 154(b) by 0 days.

(21) Appl. No.: 09/382,396

(22) Filed: Aug. 25, 1999

Related U.S. Application Data

(63) Continuation of application No. PCT/FR98/01387, filed on Jun. 29, 1998.

(30) Foreign Application Priority Data

Sep. 15, 1997 (FR) ............................................. 97 11450

(51) Int. Cl.[7] .......................... C12N 15/88; C12Q 1/68; C12P 19/34; C07H 21/02; C07H 21/04
(52) U.S. Cl. ......................... 435/458; 435/6; 435/91.1; 435/455; 435/458; 536/23.1; 536/24.5
(58) Field of Search ........................ 435/6, 91.1, 455, 435/375; 536/23.1, 24.3, 24.5

(56) References Cited

U.S. PATENT DOCUMENTS 6,020,143 A * 2/2000 St. George-Hyslop et al. .. 435/7.1

FOREIGN PATENT DOCUMENTS

| EP | 785 282 | 7/1997 |
|---|---|---|
| WO | 96/34099 | 10/1996 |
| WO | 97/08319 | 3/1997 |
| WO | 97/22695 | 6/1997 |
| WO | 97/27296 | 7/1997 |
| WO | WO 97/46678 | * 12/1997 |

OTHER PUBLICATIONS

Karen Pihl–Carey, Isis To Restructure As Crohn's Disease Drug Fails In Phase III, The Daily Biotechnology Newspaper, vol. 10, No. 239 pp. 1–2.*

Giorgio Palu' et al., In pursuit of new developments for gene therapy of human disease, Journal of Biotechnology 68 (1999) pp. 1–13.*

Andrea D. Branch, A good antisense molecule is hard to find, TIBS 23—Feb. 1998 pp. 45–50.*

Stanley T. Crooke, Antisense Research and Application, pp. 1–50.*

D.P. Huynh et al., "Neuronal Expression and Intracellular Localization of Presenilins in Normal and Alzheimer Disease Brains", J. Neuro. Exper. Neurology, vol. 56:9, 9/97, pp. 1009–1017.

R. Ward et al., "Presenilin–1 is processed into two major cleavage products in neuronal cell lines", Neurodegeneration, vol. 5:4, 12/96, pp. 293–298.

* cited by examiner

Primary Examiner—Sean McGarry
Assistant Examiner—Jane Zara
(74) Attorney, Agent, or Firm—Foley & Lardner

(57) ABSTRACT

A compound that inhibits the cellular expression of a nucleotide sequence corresponding to all or part of the presenilin 1 gene, the compound comprising an antisense molecule comprising the antisense of a polynucleotide sequence selected from the group consisting of the entire polynucleotide sequence of the presenilin 1 gene, a fragment of the sequence of the presenilin 1 gene, the promoter or other regulatory sequence of the presenilin 1 gene and a polynucleotide sequence that is at least 90% homologous to the polynucleotide sequence of the presenilin 1 gene is described. Pharmaceuticals containing and methods of inhibiting the presenilin 1 gene using such compound are also described. A compound and method of inhibiting the expression product of the presenilin 1 gene also is described. A method of treating a patient having a condition characterized by excessive cell growth also is described. A method of diagnosing cancer also is described. A method of screening drugs that inhibit the presenilin 1 gene also is described. A compound and pharmaceutical that activates the presenilin 1 gene also is described as is a method of treating diseases associated with cell death.

16 Claims, 5 Drawing Sheets

FIG. 1a

```
1961 TAGCTTTGACCGTGGGCATGGAGATTTACCCGCACTGTGAACTCTCTAAGGTAAACAAAGTGAGGTGA C *
2031 CAAACAGAGCTGCCATCTTCCACACCATGTTGGAAATAAAACCGTCCTAGCTGGAACCCTTACTGTCCCA
2101 GGAGGTTCCGTGTGGGGGTGGCACTGGGCCGGGCCTCCCTCTCAGGCTCCTTTGCTGCCCACTTGTAGT
2171 TTAAATAAGGACACCGCCCTACACAAACCTCACCCCTGTCACATCCAGTGACTCTGACCACTTTAGTTCT
2241 CAAACTCTCTCACTATTATCTGTGGTTGCCGTTTCTTCCCAAGGCCAGCCTGGACGAATTTGGGGTTGCT
2311 CTATCCTGAGAGTTGTAACCTCAACTTCCAAAGTTTATATTTTCTTGAAATGATGGATCTATTGCTCAAC
2381 AGTCCCTGTCATCCTTAAGTGACTTCTGGGTTTCCCACAAATTCCTCACTTTTAGACACACTCTAAGCTT
2451 ACTTCTGGCCTGGATGCTTCCTCTCCCTGTCTCTCCCTTGCCCCACAGCGGTTCCCTGACAGCAGACAAG
2521 GCAGCTCTGGGAGGTAGCTAGTATCCAATAACCCAGGGGTTTCCTCATGTGATGCAAATACTACGTGTC
2591 AACCAATCAGTGCTGTCAACGGGCTGCCATAGCTCCTTCGATGGCAAATAGGATGTGTGCCCAAAGAAT
2661 AAAGCGATCA GTGGCTGGTG
```

FIG. 1b

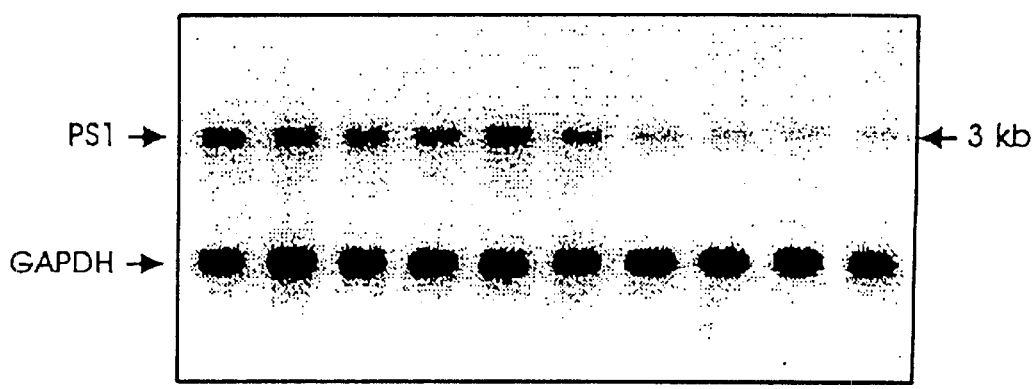

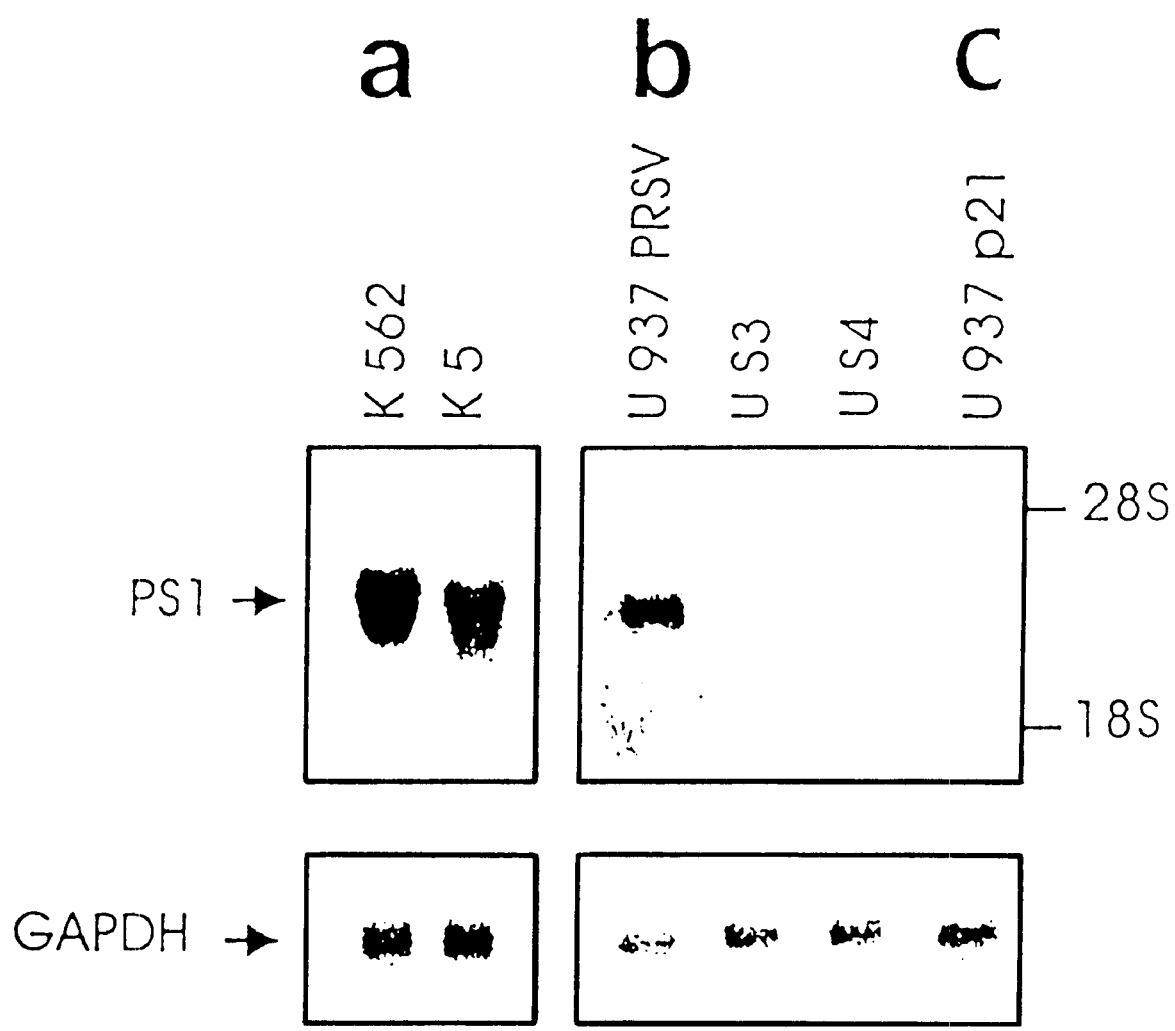

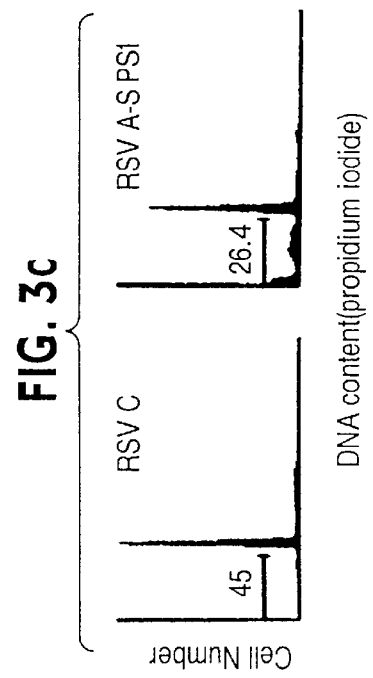
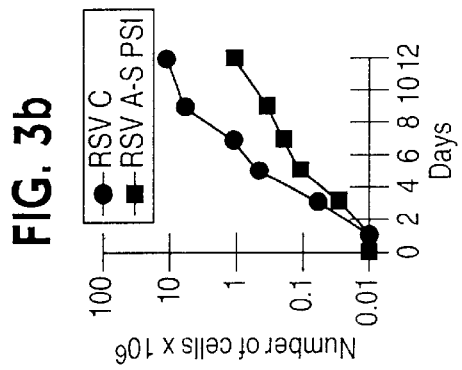
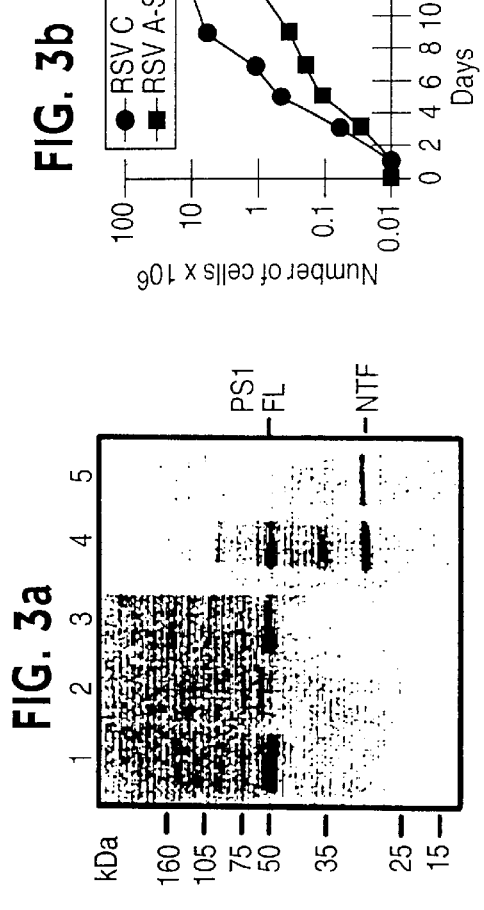
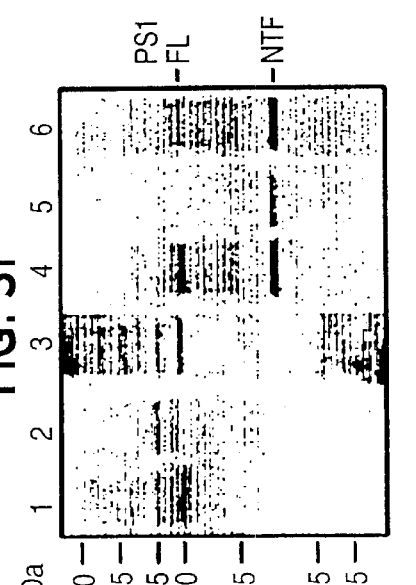
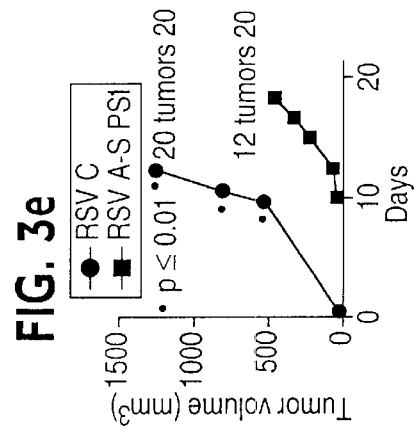
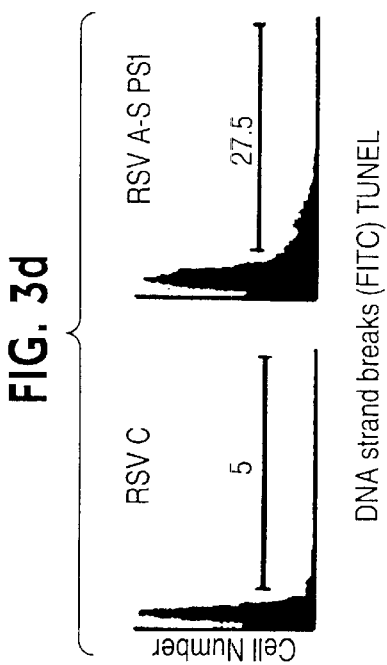

FIG. 4

TSIP2 (corresponds to Mus musculus S182)

CACCGGTGAGACCTCTAGGGCGGGGCCTAGGACGACCTGCTCCGTGGGCCGCGA
GTATTCGTCGGAAACAAAACAGCGGCAGCTGAGGCGGAAACCTAGGCTGC
GAGCCGGCCGCCCGGGCGCGGAGAGAGAAGGAACCAACACAAGACAGC
AGCCCTTCGAGGTCTTTAGGCAGCTTGGAGGAGAACACATGAGAGAAG
AATCCCAAGAGGTTTTGTTTTCTTTGAGAAGGTATTTCTGTCCAGCTGCTC
CAATGACAGAGATACCTGCACCTTTGTCCTACTTCCAGAATGCCCAGATG
TCTGAGGACAGCCACTCCAGCAGCGCCATCCGGAGCCAGAATGACAGCC
AAGAACGGCAGCAGCAGCATGACAGGCAGAGACTTGACAACCCTGAGCC
AATATCTAATGGGCGGCCCCAGAGTAACTCAAGACAGGTGGTGGAACAA
GATGAGGAGGAAGACGAAGAGCTGACATTGAAATATGGAGCCAAGCATG
TCATCATGCTCTTTGTCCCCGTGACCCTCTGCATGGTCGTCGTCGTGGCC
ACCATCAAATCAGTCAGCTTCTATACCCGGAAGGACGGTCAGCTAATCTA
CACCCCATTCACAGAAGACACTGAGACTGTAGGCAAAGAGCCCTGCACT
CGATCCTGAATGCGGCCATCATGATCAGTGTCATTGTCATTATGACCATCC
TCCTGGTGGTCCTGTATAAATACAGGTGCTACAAGGTCATCCACGCCTGG
CTTATTATTTCATCTCTGTTGTTGCTGTTCTTTTTTCGTTCATTTACTTAGG
GGAAGTATTTAAGACCTACAATGTCGCCGTGGACTACGTTACAGTAGCAC
TCCTAATCTGGAATTTTGGTGTGGTCGGGATGATTGCCATCCACTGGAAA
GGCCCCTTCGACTGCAGCAGGCGTATCTCATTATGATCAGTGCCCTCAT
GGCCCTGGTATTTATCAAGTACCTCCCCGAATGGACCGCATGGCTCATCT
TGGCTGTGATTTCAGTATATGATTTGGTGGCTGTTTATGTCCCAAAGGCC
CACTTCGTATGCTGGTTGAAACAGCTCAGGAAAGAAATGAGACTCTCTTT
CCAGCTCTTATCTATTCCTCAACAATGGTGTGGTTGGTGAATATGGCTGAA
GGAGACCCAGAAGCCCAAAGGAGGGTACCCAAGAACCCCAAGTATAACA
CACAAAGAGCGGAGAGAGAGACACAGGACAGTGGTTCTGGGAACGATGA
TGGTGGCTTCAGTGAGGAGTGGGAGGCCCAAAGAGACAGTCACCTGGGG
CCTCATCGCTCCACTCCCGAGTCAAGAGCTGCTGTCCAGGAACTTTCTGG
GAGCATTCTAACGAGTGAAGACCCGGAGGAAAGAGGAGTAAAACTTGGA
CTGGGAGATTTCATTTTCTACAGTGTTCTGGTTGGTAAGGCCTCAGCAAC
CGCCAGTGGAGACTGGAACACAACCATAGCCTGCTTTGTAGCCATACTGA
TCGGCCTGTGCCTTACATTACTCCTGCTCGCCATTTTCAAGAAAGCGTTGC
CAGCCCTCCCCATCTCCATCACCTTCGGGCTCGTGTTCTACTTCGCCACG
GATTACCTTGTGCAGCCCTTCATGGACCAACTTGCATTCCATCAGTTTTAT
ATCTAGCCTTTCTGCAGTTAGAACATGGATGTTTCTTCTTTGATTATCAAA
AACACAAAAACAGAGAGCAAGCCCGAGGAGGAGACTGGTGACTTTCCTG
TGTCCTCAGCTAACAAAGGCAGGACTCCAGCTGGACTTCTGCAGCTTCCT
TCCGAGTCTCCCTAGCCACCCGCACTACTGGACTGTGGAAGGAAGCGTCT
ACAGAGGAACGGTTTCCAACATCCATCGCTGCAGCAGACGGTGTCCCTCA
GTGACTTGAGAGACAAGGACAAGGAAATGTGCTGGGCCAAGGAGCTGCC
GTGCTCTGCTAGCTTTGACCGTGGGCATGGAGATTTACCCGCACTGTGAA
CTCTCTAAGGTAAACAAAGTGAGGTGAACCAAACAGAGCTGCCATCTTCCACA
CCATGTTGGAAATAAAACCGTCCTAGCTGGAACCCTTACTGTCCCAGGAGGTTCCG
TGTGGGGGTGGCACTGGGCCGGGCCTCCTCTCAGGCTCCTTTGCTGCCCACTTGT
AAGTTTAAATAAGGACACCGCCCTACACAAACCTCACCCCTGTCACATCCAGTGACT
CTGACCACTTTAGTTCTCAAACTCTCTCACTATTATCTGTGGTTGCCGTTTCTTCCCA
AGGCCAGCCTGGACGAATTTGGGGTTGCTCTATCCTGAGAGTTGTAACCTCAACTT
CCAAAGTTTATATTTTCTTGAAATGATGGATCTATTGCTCAACAGTCCCTGTCATCCT
TAAGTGACTTCTGGGTTTCCCACAAATTCCTCACTTTTAGACACACTCTAAGCTTACT
TCTGGCCTGGATGCTTCCTCTCCCTGTCTCTCCCTTGCCCCACAGCGGTTCCCTGAC
AGCAGACAAGGCAGCTCTGGGAGGTAGCTAGTATCCAATAACCCAGGGGTTTCCTC
ATGTGATGCAAATACTACGTGTCC<u>AACCAATCAGTGCTGTCAACGGGCTGCCATAG
CTCCTTCGATGGCAAATAGGATGTGTGCCCAAAGAATTAAAGCGATCAGTGGCTGG
TG</u>

COMPOUND AND METHODS OF INHIBITING OR STIMULATING PRESENILIN 1 AND RELATED PHARMACEUTICALS AND DIAGNOSTIC AGENTS

CROSS REFERENCE TO RELATED APPLICATIONS

This application is a continuation of PCT/FR98/01387, filed Jun. 29, 1998, which in turn, claims priority to French Patent Application No. 97 11450, filed Sep. 15, 1997.

FIELD OF INVENTION

The invention relates to methods and compounds for inhibiting or stimulating presenilin 1 and related pharmaceuticals and diagnostic agents.

BACKGROUND OF INVENTION

Since the discovery of the presenilins in 1995, a significant effort has been made to understand their function and to associate them with a well-defined molecular scheme, especially that involved in programmed cell death. All of this suggests that the presenilins are "genes for life and death". PS1 and PS2 are integral membrane proteins with 6 to 9 transmembrane domains situated in the endoplasmic reticulum and the early Golgi complex. PS1 is strongly homologous to PS2.

It has recently been demonstrated that the genes of presenilin 1 and 2 were involved in the molecular phenomena at the root of familial Alzheimer's disease. Non-sense mutations in the presenilin 1 gene (PS1) have been found in the most aggressive form of familial early onset Alzheimer's disease, especially intervening at an early stage in the disease (Sherrington et al., Nature 375: 754–760 (1995), herein incorporated by reference).

The product of the presenilin 2 gene forms stable complexes with precursor proteins of beta-amyloid. Beta-amyloid is the principle molecule formed in typical plaques appearing in people suffering from Alzheimer's disease. For PS1, mutant transgenic mice show a high level of the 42 precursor protein of beta-amyloid, there even supplying a functional link with what takes place in Alzheimer's disease. The intracellular expression of beta-amyloid proteins under a specific promoter of the neurons in transgenic mice leads to neurodegeneration and increased expression of p53 has been observed in some of these lesions. The overexpression of PS2 in the differentiated PC12 cells of nerve growth factor increases apoptosis initiated by the elimination of trophic factors. In addition, mutations in PS2 could induce apoptosis, even with elimination of trophic factors. During development, anomalies of the skeletons and of the central nervous system appear in presenilin 1-deficient mice. In addition, PS1 is necessary for the expression of Notch 1 and of DLL1 in the development of the paraxial mesoderm. The presenilin proteins seem to show a complex alternative cleavage during apoptosis. PS1 seems to be an active member of the molecular pathways p53-p21 Waf1 of apoptosis and of tumoral suppresion and it is important to recall that expression of intact p53 is necessary to ensure the complex functions of the central nervous system.

To this date, a series of cDNA molecules regulated by p53 during apoptosis and tumoral suppresion have been identified in WO-A-97/22695, which is herein incorporated by reference. The cDNAs were cloned by differential analysis of the mRNAs. TSIP2 (Tumour Suppressor Inhibited Pathway Clone 2) was cloned in a fragment of 90 bp. Used as a probe, the cDNA of TSIP2 revealed two bands by means of Northern blot analysis, one a strong one of 3 kb and the other a weaker one of 7 kb. These mRNAs are inhibited after expression of the wild-type p53 function. This model system takes advantage of the val-135 mutant of p53, which is sensitive to temperature, stably transfected in M1 myeloid cells. In one of these transfectants, exemplified by the LTR 6 cells, 37 to 32° C. passage induces the expression of a functional wild-type p53 resulting in an apoptosis phenomenon. The cDNA fragment of TSIP2 initially of 90 bp cloned at the start did not have any homology with any sequence known in the data bases. This fragment was extended to the whole of the cDNA using an RACE-PCR. After sequencing of an additional fragment of 700 bp, it turned out that TSIP2 was identical to the PS1 gene of mice. The inventors have discovered that the inhibition of the expression of the mRNA of PS1 was confirmed by a Northern blot analysis using the cDNA probe in its entirety in the M1-LTR6 model. Regulation intervenes very rapidly after passage at 32° C. and is indubitable after induction of wild-type p53 for two hours. This indicates that the modulation of the expression of PS1 intervenes at an early stage of the cell death programme, when no cell has yet died of apoptosis.

SUMMARY OF THE INVENTION

The present invention is based on the discovery that inhibition of PS1 by p53 or p21 or a molecule, such as an antisense molecule, induces apoptosis (cell death). Accordingly, it is possible to treat diseases associated with excessive cell growth, such as cancer, by inhibiting PSI expression. Another aspect of the invention is based on the discovery that wild type PSI inhibits p53 induced apoptosis. Accordingly, it is possible to treat diseases wherein it is desirable to inhibit cell death by stimulating the PS1 gene or inhibiting p53 or p21.

Thus, one embodiment of the invention relates to a compound that inhibits the cellular expression of a nucleotide sequence corresponding to all or part of the presenilin 1 gene, said compound comprising an antisense molecule comprising the antisense of a polynucleotide sequence selected from the group consisting of the entire polynucleotide sequence of the presenilin 1 gene, a fragment of the sequence of the presenilin 1 gene, the promoter or other regulatory sequence of the presenilin 1 gene and a polynucleotide sequence that is at least 90% homologous to the polynucleotide sequence of the presenilin 1 gene. This compound may be an antisense molecule comprising the antisense of the sequence of FIG. 4, or a fragment thereof, preferably a cDNA antisense.

In another embodiment, the invention relates to a compound that binds the product of the presenilin 1 gene comprising an antibody that specifically binds said product.

In another embodiment, the invention relates to a compound for inhibiting the cellular expression of the presenilin 1 gene comprising a molecule that activates p53 or p21.

Another embodiment relates to a method of treating a patient having a condition characterized by excessesive cell growth, comprising administering to a patient a cell growth inhibiting amount of a compound, wherein in an in vitro bioassay said compound inhibits the expression of the presenilin 1 gene.

In another embodiment, the invention relates to a compound that stimulates the cellular expression of a nucleotide sequence corresponding to all or part of the presenilin 1 gene.

In another embodiment, the invention relates to a compound that activates the cellular expression of the presenilin 1 gene by interfering with the metabolic pathway of p53 or p21. This compound may be an antibody that binds p53 or p21.

In another embodiment, the invention relates to a method of inhibiting apoptosis in cells comprising transfecting said cells with an expression vector comprising the polynucleotide sequence of the presenilin 1 gene, a fragment of the sequence of the presenilin 1 gene or a polynucleotide sequence that is at least 90% homologous to the polynucleotide sequence of the presenilin 1 gene.

Another embodiment relates to a pharmaceutical composition comprising an expression vector comprising the polynucleotide sequence of the presenilin 1 gene, a fragment of the sequence of the presenilin 1 gene or a polynucleotide sequence that is at least 90% homologous to the polynucleotide sequence of the presenilin 1 gene.

Another embodiment relates to a method of detecting the presence of the presenilin 1 gene in a mammalian tissue sample, the method comprising the steps of:

(a) contacting said tissue sample with a cDNA fragment of TSIP 2 or with the above desribed molecule that binds the presenilin 1 gene under conditions of hybridization, and (b) detecting the formation of a hybrid of said molecule with the presenilin 1 gene.

In yet another embodiment, the invention relates to a method of screening for drugs that cause cell death comprising contacting a drug with the presenilin 1 gene and detecting whether the drug inhibits expression of said gene, wherein inhibition of expression indicates the drug's potential use in causing cell death.

DESCRIPTION OF FIGURES

FIG. 1a (SEQ ID NO:1) shows that the extension of the cDNA fragment of TSIP2 (underlined) to the clone of total length shows the molecule is identical to PS1 (the asterisk indicates the position of the stop codon).

FIG. 1b shows the downstream regulation of PS1 by wild-type p53 in the M1 LTR 6 model. Northern blot analysis shows the inhibition of the expression (down regulation) of PS1 once the wild-type p53 function is activated by bringing the culture to 32° C. at different time intervals (the whole of the cDNA of PS1 is used as a probe).

FIGS. 2a–2c show that a Northern blot analysis indicating the downstream regulation of PS1 in various models of tumoral suppresion and of apoptosis (the whole of the cDNA of PS1 is used as a probe). FIG. 2a shows the results of a Northern blot analysis in the K562-KS systems, when wild-type p53 is reexpressed in the KS cells; FIG. 2b shows the results of a Northern blot analysis in the U937-US system (3 and 4), when p21 Waf is reexpressed in the US cells; FIG. 2c shows the results in the stable p21 Waf1 transfectants of the U937 cells.

FIGS. 3a–3f show the biological effects of the repression of PS1 in the U937 cells. FIG. 3a depicts the results of a Western blot analysis with anti-PS1 antibodies. Bands 1 to 3: use of a PS1 anti-C-terminal end polyclonal antibody. Band 1: U937 cells. Band 2: U937 cells stably transfected with the cDNA of an anti-sense strand of PS1 (RSV A-S PS1). Band 3: U937 cells transfected with the control vector alone (RSV C). Bands 4 and 5: use of an anti-N-terminal end monoclonal antibody of PS1. Band 4: U937 cells transfected with the control vector alone (RSV C). Band 5: U937 cells stably transfected with the cDNA of the anti-sense strand of PS1 (RSV A-S PS1). FL indicates the product of the protein PS1 of 50 kDa in its total length or "full length" and NTF indicates the N-terminal fragment of PS1 of 30 kDa. FIG. 3b is a Growth curve of U937 cells transfected with the vector alone (-●-RSV C) and U937 cells transfected with the anti-sense vector of PS1 (-■-RSV A-S Ps1). FIG. 3c is a FACS analysis of the content of DNA in the U937 cells transfected with the vector alone (RSV C) and cells transfected with the anti-sense strand of PS1 (RSV A-S PS1). 4.5% and 26.4% of the cell population respectively are in the pre-G1 phase. FIG. 3d, a FACS analysis of the TUNEL test, shows that 5% of the U937 cells transfected with the vector alone (RSV C) are positive, in comparison with the 27.5% of positive cells among the U937 cells transfected with the anti-sense strand of PS1 (RSV A-S PS1). FIG. 3e shows that in the tumorigenicity test in scid/scid mice after injection of U937 cells transfected with the control vector alone (-●-RSV C) gives rise to significant tumours localized in 20 sites situated outside of the 20 injection sites, the said tumours being apparent at an early stage. The U937 cells stably transfected with the cDNA of the anti-sense strand of Ps1 (-■-RSV A-S PS1) give rise to smaller tumours which appear later at a level of 12 out of 20 injection sites. * indicates the statistical significance: $p \leq 0.001$. FIG. 3f shows the results of a Western blot analysis using anti-PS1 antibodies. Bands 1 to 3: use of the anti-C-terminal end polyclonal antibody of PS1. Band 1: U937 cells transfected with the control vector alone (RSV C). Band 2: U937 cells transfected with the anti-sense strand of PS1 (RSV A-S PS1), this shows that the band corresponding to 50 kDa is no longer detectable. Band 3: extract of proteins from tumours which have occurred in animals in which U937 cells transfected with the anti-sense strand of PS1 (RSV A-S PS1) have been injected, this shows a reexpression of the 50 kDa protein. Bands 4 to 6: use of the anti-N-terminal end monoclonal antibody. Band 4: U937 cells transfected with the control vector alone (RSV C). Band 5: U937 cells transfected with the anti-sense strand of PS1 (RSA A-S PS1). Band 6: extract of proteins from tumours occurring in animals into which U937 cells transfected with the anti-sense strand of PS1 (RSV A-S PS1) have been injected, this shows a reexpression of the 50 kDa protein (FL) and of the N-terminal fragment of 30 kDa (NTF).

FIG. 4 is the nucleotide sequence of TSIP2 (SEQ ID NO: 2). The sequence appearing in bold characters corresponds to a sequence having 100% identity with Mus musculus S182, which is the murine homologue of the human presenilin 1 gene.

DETAILED DESCRIPTION OF THE INVENTION

Figure 5A:
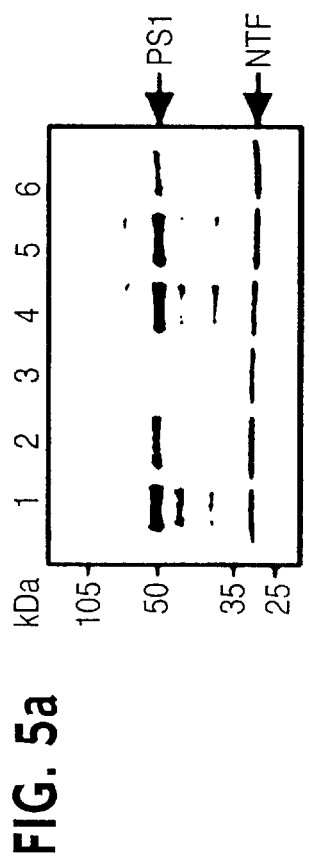
FIG. 5a shows the results of a Western blot analysis with anti-PS1 antibodies. LTR-6 cells at 37 degrees centigrade (lane 1), and after 12 hours (lane 2), and after 24 hours (lane 3) at 32 degrees centigrade. LTR-6 cells transfected with PS1 (LTR-PS1) at 37 degrees centigrade (lane 4) and after 12 hours (lane 5) and after 24 hours (lane 6) at 32 degrees centigrade. PS1 indicates the full length 50 kDa PS1 protein product and NTF the 30 kDa N-terminal fragment of PS1.

Thus, in one embodiment, the present invention relates to a compound that inhibits the cellular expression of a nucleotide sequence corresponding to all or part of the presenilin 1 gene. This compound may be a small molecule or a synthetic ligand such a peptide nucleic acid, a hairpin polyamide or an antisense molecule. See, e.g., Good and Nielsen, *Nature Biotechnology*, 16: 355–358 (1998); Gottesfeld et al., *Nature* 387: 202–205 (1997), all of which are herein incorporated by reference. In one embodiment, this compound comprises an antisense molecule comprising the antisense of a polynucleotide such as the entire polynucleotide sequence of the presenilin 1 gene, a fragment of the sequence of the presenilin 1 gene, the promoter or other regulatory sequence of the presenilin 1 gene or a polynucleotide sequence that is at least 90% homologous to the polynucleotide sequence of the presenilin 1 gene.

Given the known sequence of the presenilin 1 gene and its associated control elements, certain presenilin-1-specific inhibitors of expression may be rationally designed. Most commonly, these inhibitors will be relatively small RNA or DNA molecules because they can be designed to be highly specific. In general, so-called "antisense" molecules will have a sequence which is complementary to a portion of the presenilin 1 DNA or mRNA, preferably the pre-mRNA, i.e., the pre-splicing version. One particularly preferred class of antisense molecules is directed to the control elements for splicing and/or translation. Such "translational control elements" include the very 5' end of the mRNA (where the ribosome associates with the mRNA) and the translational start site (an ATG, from the non-coding DNA perspective). The "splicing control elements" include the splice junctions. It may also be advantageous to direct antisense molecules to introns themselves, especially those near the 5' end of the gene.

As indicated, the antisense molecules can have a variety of chemical constitutions, so long as they retain the ability specifically to bind at the indicated control elements. Thus, especially preferred molecules are oligo-DNA, RNA and protein nucleic acids (PNAs). The oligonucleotides of the present invention can be based, for example, upon ribonucleotide or deoxyribonucleotide monomers linked by phosphodiester bonds, or by analogues linked by methyl phosphonate, phosphorothioate, or other bonds. These can be engineered using standard synthetic techniques to specifically bind the targeted control region(s). While these molecules may also be large, they are preferably relatively small, i.e., corresponding to less than about 50 nucleotides, more preferably less than about 25 nucleotides. Such oligonucleotides may be prepared by methods well-known in the art, for instance using commercially available machines and reagents available from Perkin-Elmer/Applied Biosystems (Foster City, Calif.).

Phosphodiester-linked oligonucleotides are particularly susceptible to the action of nucleases in serum or inside cells, and therefore in a preferred embodiment the oligonucleotides of the present invention are phosphorothioate or methyl phosphonate-linked analogues, which have been shown to be nuclease-resistant. See Stein et al., Phosphorothioate Oligodeoxynucleotide Analogues in "Oligodeoxynucleotides—Antisense Inhibitors of Gene Expression" Cohen, Ed. McMillan Press, London (1988). Persons knowledgeable in this field will be able to select other linkages for use in the present invention.

The relative activity of antisense oligonucleotides directed against a specific gene is generally inversely proportional to its location relative to the AUG start codon of the target gene. Accordingly, it is preferred that an antisense oligonucleotide targeted at a specific presenilin-1 gene sequence be chosen such that the oligonucleotide hybridizes within approximately 25 bases of the AUG start codon of the gene.

To select the preferred length for an antisense oligonucleotide, a balance must be struck to gain the most favorable characteristics. Shorter oligonucleotides 10–15 bases in length readily enter cells, but have lower gene specificity. In contrast, longer oligonucleotides of 20–30 bases offer superior gene specificity, but show decreased kinetics of uptake into cells. See Stein et al. (1988), supra. This invention contemplates using oligonucleotides approximately 14 to 25 nucleotides long.

Antisense molecules can be delivered in a variety of ways. They may be synthesized and delivered as a typical pharmaceutical, usually parenterally. They may be formulated as detailed below, but one preferred formulation involves encapsulation or association with cationic liposomes. They may be modified with a targeting sequence, and optionally linked to a polyamine, such a polylysine, as described above. See Bachmann et al., *J. Mol. Med.* 76:126–32 (1998) for one approach to delivering antisense molecules using a targeting sequence. Alternatively, antisense molecules may be delivered using gene therapy methods, detailed below. Using gene therapy vectors, single, or multiple tandem copies of antisense molecules can be used.

Administration of an antisense oligonucleotide to a subject can be effected orally or by subcutaneous, intramuscular, intraperitoneal, or intravenous injection. Pharmaceutical compositions of the present invention, however, are advantageously administered in the form of injectable compositions. A typical composition for such purpose comprises a pharmaceutically acceptable solvent or diluent and other suitable, physiologic compounds. For instance, the composition may contain oligonucleotide and about 10 mg of human serum albumin per milliliter of a phosphate buffer containing NaCl.

As much as 700 milligrams of antisense oligodeoxynucleotide has been administered intravenously to a patient over a course of 10 days (i.e., 0.05 mg/kg/hour) without signs of toxicity. Sterling, "Systemic Antisense Treatment Reported," *Genetic Engineering News* 12: 1, 28 (1992).

Another nucleic-acid-based method for down-regulating presenilin 1 gene expression utilizes "ribozymes." Ribozymes are small RNA molecules that characteristically bind a specific, complementary RNA sequence (i.e., presenilin-1 mRNA) and cleave the bound target at a specific site. Technology for the design and manufacture of ribozymes is known in the art. See, for example, Haseloff et al., U.S. Pat. Nos. 5,574,143 (1996), 5,589,580 (1996) and 5,432,508 (1996), and Kramer et al. U.S. Pat. No. 5,616,459 (1997) which are hereby incorporated by reference in their entirety.

In one embodiment, the present invention contemplates the use of a polynucleotide sequence that is at least 90% homologous to the open reading frame of the presenilin 1 gene or to a polynucleotide that is at least 50% homologous to the entire sequence of the presenilin 1 gene. In this context, "homology" connotes a similarity between two nucleic acid sequences that is short of identity, but is indicative of an evolutionary relationship between the sequences. In general, both the DNA and protein molecules of the invention can be defined with reference to "sequence identity." As used herein, "sequence identity" refers to a comparison made between two molecules using standard algorithms well known in the art. Although any sequence algorithm can be used to define "sequence identity," for clarity, the present invention defines identity where the open reading frame of the preseline 1 gene is used as the reference sequence to define the percentage identity of polynucleotide homologues over its length. The choice of parameter values for matches, mismatches, and inserts or deletions is arbitrary, although some parameter values have been found to yield more biologically realistic results than others. Methods of comparing sequences are set forth in George et al., "Macromolecular Sequencing and Synthesis" *Selected Methods and Applications*, pp. 127–149, Alan R. Liss, Inc. (1988), which is incorporated herein by reference.

Among the agents capable of inhibiting all or part of the presenilin 1 gene or of a strongly homologous nucleotide sequence, the present invention comprises the use of an anti-sense nucleotide sequence of that of FIG. 4.

In the case where it is a question of inhibiting the action of the expression product of the abovementioned sequences, that is to say of the peptide sequence corresponding to the sequences in question, the invention comprises the use of an antibody, preferably monoclonal, directed against the expression product of the preseline 1 gene.

Antibodies are produced using techniques well known in the art. The preparation of polyclonal antibodies is well-known to those of skill in the art. See, for example, Green et al., "Production of Polyclonal Antisera," in IMMUNOCHEMICAL PROTOCOLS (Manson, ed.), pages 1–5 (Humana Press 1992).

Alternatively, an antibody of the present invention may be derived from a rodent monoclonal antibody (MAb). Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1–2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1–2.7.12 and pages 2.9.1–2.9.3. Also, see Baines et al., "Purification of Immunoglobulin G (IgG)," in METHODS IN MOLECULAR BIOLOGY, VOL. 10, pages 79–104 (The Humana Press, Inc. 1992).

An antibody of the present invention may also be derived from a subhuman primate antibody. General techniques for raising therapeutically useful antibodies in baboons may be found, for example, in Goldenberg et al., international patent publication No. WO 91/11465 (1991), and in Losman et al., *Int. J. Cancer* 46: 310 (1990), which is incorporated by reference.

Alternatively, a therapeutically useful antibody may be derived from a "humanized" monoclonal antibody. Humanized monoclonal antibodies are produced by transferring mouse complementary determining regions from heavy and light variable chains of the mouse immunoglobulin into a human variable domain, and then, substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993), each of which is hereby incorporated by reference.

As an alternative, an antibody of the present invention may be derived from human antibody fragments isolated from a combinatorial immunoglobulin library. See, for example, Barbas et al., *METHODS: A Companion to Methods in Enzymology* 2: 119 (1991), and Winter et al., *Ann. Rev. Immunol.* 12: 433 (1994), which are incorporated by reference. Cloning and expression vectors that are useful for producing a human immunoglobulin phage library can be obtained, for example, from STRATAGENE Cloning Systems (La Jolla, Calif.).

In addition, an antibody of the present invention may be derived from a human monoclonal antibody. Such antibodies are obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7: 13 (1994), Lonberg et al., *Nature* 368: 856 (1994), and Taylor et al., *Int. Immun.* 6: 579 (1994), which are incorporated by reference.

Antibody fragments can be prepared by proteolytic hydrolysis of the antibody or by expression in *E. coli* of the DNA coding for the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1–2.8.10 and 2.10.–2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody. For example, Fv fragments comprise an association of $V_H$ and $V_L$ chains. This association can be noncovalent, as described in Inbar et al., *Proc. Nat'l Acad. Sci. USA* 69: 2659 (1972). Alternatively, the variable chains can be linked by an intermolecular disulfide bond or cross-linked by chemicals such as glutaraldehyde. See, for example, Sandhu, supra.

Preferably, the Fv fragments comprise $V_H$ and $V_L$ chains which are connected by a peptide linker. These single-chain antigen binding proteins (sFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing sFvs are described, for example, by Whitlow et al., *Methods: A Companion to Methods in Enzymology* 2: 97 (1991). Also see Bird et al., *Science* 242:423–426 (1988), Ladner et al., U.S. Pat. No. 4,946,778, Pack et al., *Bio/Technology* 11:1271–1277 (1993), and Sandhu, supra. Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991).

Thus, the present invention is, in one embodiment, directed to a method of interfering with the biological pathway of the presenilin 1 gene by binding to its exression product to an antibody that has been raised against such product.

In another embodiment, the present invention is directed to a method of treating a patient having a condition characterized by excessive cell growth, such as a tumor or cancer, comprising contacting the cells or tumor with a therapeutically effective amount of a compound, wherein in an in vitro bioassay, the compound inhibits cell growth or leads to apoptosis. Such bioassays or human model systems include the TUNEL assay discussed below.

In other embodiments, the invention is directed to a compound for inhibiting the cellular expression of the presenilin 1 gene comprising a compound that activates p53 or p21.

Another aspect of the invention relates to a compound that activates the cellular expression of the presenilin 1 gene. This compound may activate PS1 by interfering with the metabolic pathway of p53 or p21. In one embodiment, such a compound is an antibody against p53 or p21.

The above described inventions are based on the inventors' discovery that that PS1 is regulated downstream in a p53 model of apoptosis. They analysed whether a similar scheme of the inhibition of the expression of PS1 was conserved in other models of tumoral suppression and to investigate the biological pertinence of this downstream regulation.

To investigate the significance of the inhibition of PS1 in the phenomena of apoptosis and of tumoral suppression, the expression of PS1 has been analysed in a series of human model systems with reexpression either of wild-type p53 or of p21 Waf1. The KS cells come from the human erythroleukaemic K562 line of cells. These KS cells constitutively express wild-type p53 and this is detectable at a protein level, whereas the parent K562 cells do not express p53. The regulation of PS1 is observed in the KS1 cells which have the suppressed malignant phenotype (FIG. 2a) . PS1 is also regulated in the US cells which come from a single clone of a U937 human monocytic leukaemia (FIG. 2b)). The US cells have the characteristic of reexpressing p21 Waf1 independently of p53. These cells likewise have the strongly suppressed malignant phenotype. P21 Waf1 is part of the series of molecules of which it has been determined that it is activated by p53 but which can be likewise expressed independently in an alternative route to p53. The regulation of the expression of PS1 by p21 Waf1 was then confirmed in stable transfectants of U937 cells with p21 Waf1 (FIG. 2c)). These experiments suggest that PS1 is effectively regulated downstream by the activation of p53 and/or p21 Waf1 in apoptosis and tumoral suppression.

Consequently, as described above, the present invention relates to an agent inhibiting cellular expression of a nucleotide sequence in accordance with the invention, and preferably of PS1, by the activation of the metabolic pathway of p53 and/or by the metabolic pathway of p21, this being with the aim of inducing cell death. However, the present invention also relates to a compound that activates the cellular expression of a nucleotide sequence in accordance with the invention, and preferably of PS1, by inhibition of the metabolic pathway of p53 and/or the metabolic pathway of p21, this with the aim of preventing cell death. This compound preferably would be in a pharmaceutical composition. Most preferably this compound would be an antibody against against p53 or p21, which would be produced according to methods well-known in the art, as set forth above. This pharmaceutical could be used in the treatment of diseases associated with cell death, such as neurodegenerative or viral-related diseases.

Finally, with the aim of investigating the impact of the regulation of PS1 on cell growth, apoptosis and the malignant phenotype, the U937 cells were transfected with cDNA of anti-sense PS1. FIG. 3a) shows the inhibition of the expression of the PS1 protein in stable U937 transfectants by the anti-sense strand of PS1. The anti-C-terminal end polyclonal antibody of PS1 detects the full length protein of PS1 of 50 kDa (Sherrington R. et al. Cloning of a gene bearing missense mutations in early-onset familial Alzheimer's disease. *Nature* 375, 754–760 (1995); Kovacs D. M., et al. Alzheimer-associated presenilin 1 and 2: Neuronal expression in brain and localization to intracellular membranes in mammalian cells. *Nature Medicine* 2, 224–229 (1996)) but does not allow the proteolytic products to be detected under the experimental conditions (FIG. 3a, bands 1 and 3). The 50 kDa band is absent in the U937 cells transfected with the anti-sense strand of PS1 (FIG. 3a, band 2). With a monoclonal antibody directed against the N-terminal fragment of PS1 under specific experimental conditions comprising protein extractions in 1% NP40 and 1% Triton X-100 followed by heating in an SDS sample buffer at 56° C. for 20 minutes in 8M urea, a 50 kDa fragment was detected in the control band of U937 transfectants, as well as, as expected (Thinakaran G., et al. Endoproteolysis of Presenilin 1 and Accumulation of Processed derivatives in vivo. *Neuron* 17, 181–190 (1996)), a predominant N-terminal fragment of 30 kDa (FIG. 3a, band 4). In the U937 cells transfected with the cDNA of the anti-sense strand of PS1, the 50 kDa band is almost totally absent while the 30 kDa band is strongly suppressed (FIG. 3a, band 5). These experiments indicate that, in fact, the anti-sense construction of PS1 is effective on the inhibition of the expression of presenilin 1. The full length DNA was sequenced from U937 cells in order to known whether the anti-sense strand of PS1 blocked the expression of wild-type PS1 or the protein of a mutant of PS1, such as described in Alzheimer's disease. A detailed analysis of the sequence indicates that there is no mutation in the cDNA of PS1 in the U937 cells (data not shown). It has additionally been shown (FIG. 3b) that there is a factor 10 between the growth curve (logarithmic scale) of the U937 cells transfected with the control vector (RSV C) and that corresponding to the cells transfected with the anti-sense strand of PS1 (RSV A-S PS1). The profile or the determination of propidium iodide (FIG. 3c) indicates that the U937 cells transfected with the control vector alone (RSV C) have 4.5% of the population with a DNA in pre-G1, whereas the U937 cells transfected with the anti-sense strand of PS1 (RSV A-S PS1) have 26.4% of their population in pre-G1.

To determine whether the regulation of PS1 favours apoptosis, the Terminal Deoxynucleotidyl-transferase-Mediated UTP-biotin Nick End Labelling test (TUNEL) was carried out (FIG. 3d). The U937 transfectants for the anti-sense strand of PS1 (RSV A-S PS1) have 27.5% of their population positive for the TUNEL test while the U937 cells transfected with the vector alone (RSV C) are only 5% positive for the TUNEL test. It is to be underlined that when they were tested for their tumorigenicity in scid/scid mice, these cells, with the suppressed PS1 (RSV A-S PS1), showed a strongly suppressed malignant phenotype (FIG. 3e). All the animals into which U937 cells transfected with the control vector alone (RSV C) were injected developed significant tumours and were sacrificed in the two or three weeks following injection.

On the contrary, the mice into which the transfectants for the anti-sense cDNA of PS1 were injected developed small tumours which only became apparent after a long period and only at the level of 12 sites of injection out of 20. These animals were monitored for a period of greater than two months without showing the formation of additional tumours. The potential mechanism by which these tumours escaped the tumour-suppressor effect of the regulation of PS1 was the subject of additional investigations. PCR analysis indicates that the construct with the anti-sense strand of PS1 is still integrated into the genome (data not shown). However, this does not exclude that this is not at all functional in these tumour cells. In fact, Western blot analysis (FIG. 3f) using anti-C-terminal end polyclonal antibodies of PS1 indicates that, while the cells subjected to an injection (RSV A-S PS1) do not express any 50 kDa PS1 protein (FIG. 3f, band 2) the tumour cells reexpress it (FIG. 3f, band 3). Using the anti-N-terminal end monoclonal antibody of PS1, it is confirmed that the 50 kDa protein and the predominant 30 kDa protein are reexpressed (FIG. 3f, band 6). These data prove that the suppression of PS1 favours a reduction of growth, apoptosis and the suppression of tumours, while the reexpression of PS1 is associated with the formation of tumours.

Thus, in yet another embodiment, the invention relates to a method of screening for drugs that cause cell death comprising contacting a drug with the presenilin 1 gene and detecting whether the drug inhibits expression of said gene, wherein inhibition of expression indicates the drug's potential use in causing cell death. The presenilin 1 gene may be in U937 cells, as described above.

The present invention thus likewise relates to the use of a compound ensuring the inhibition:

a) of the cellular expression of a nucleotide sequence corresponding to all or part of the presenilin 1 gene, or b) of the cellular expression of a nucleotide sequence having at least 90% homology with a nucleotide sequence according to a), or c) of the action of the expression product of a sequence according to a) or b)

to favour the reduction of cell growth, the increase in apoptosis and/or the suppression of tumours.

Finally, in view of the above, if the inhibition of the nucleotide sequence corresponding to PS1, to the sequences related to PS1 or of the expression product of the said sequences especially favours the increase in apoptosis, it is clear that, in reverse, the said sequences and expression products can be used in the context of the present invention for anti-apoptotic purposes. Thus, the present invention likewise relates to the use:

1) a) of a nucleotide sequence corresponding to all or part of the presenilin 1 gene, or b) of a nucleotide sequence having at least 90% homology with a nucleotide sequence according to a); or 2) of an activator agent of cellular expression of a nucleotide sequence such as mentioned above, for anti-apoptotic purposes. In other words, in another embodiment, the invention is directed to a method of inhibiting apoptosis in cells comprising transfecting the cells with an expression vector comprising the polynucleotide sequence of the presenilin 1 gene, a fragment of the sequence of the presenilin 1 gene or a polynucleotide sequence that is at least 90% homologous to the polynucleotide sequence of the presenilin 1 gene. This method contemplates the construction of a vector containing the presenilin gene or a fragment thereof or a polynucleotide sequence that is at least 90% homologous to the open reading frame of the preseniling gene and the introduction of the recombinant vector into a cell.

The construction of a recombinant vector containing such the DNA according to the invention can be achieved by any of the methods well-known in the art for the insertion of exogenous DNA into a vector. See, e.g., Maniatis et al., *Molecular Cloning* (Cold Spring Harbor Press 2d ed. 1989), which is incorporated herein by reference. In addition, the prior art teaches various methods of introducing exogenous genes into cells in vivo. See Rosenberg et al., *Science* 242:1575–1578 (1988) and Wolff et al., *PNAS* 86:9011–9014 (1989), which are incorporated herein by reference. The routes of delivery include systemic administration and administration in situ. Well-known techniques include systemic administration with cationic liposomes, and administration in situ with viral vectors. Any one of the gene delivery methodologies described in the prior art is suitable for the introduction of a recombinant vector containing the DNA according to the invention into a cell. A listing of present-day vectors suitable for the purpose of this invention is set forth in Hodgson, *Bio/Technology* 13: 222 (1995), which is incorporated by reference.

For example, liposome-mediated gene transfer is a suitable method for the introduction of a recombinant vector containing the DNA according to the invention into a cell. The use of a cationic liposome, such as DC-Chol/DOPE liposome, has been widely documented as an appropriate vehicle to deliver DNA to a wide range of tissues through intravenous injection of DNA/cationic liposome complexes. See Caplen et al., *Nature Med.* 1:39–46 (1995) and Zhu et al., *Science* 261:209–211 (1993), which are herein incorporated by reference. Liposomes transfer genes to the target cells by fusing with the plasma membrane. The entry process is relatively efficient, but once inside the cell, the liposome-DNA complex has no inherent mechanism to deliver the DNA to the nucleus. As such, most of the lipid and DNA gets shunted to cytoplasmic waste systems and is destroyed. The obvious advantage of liposomes as a gene therapy vector is that liposomes contain no proteins, which thus minimizes the potential of host immune responses.

As another example, viral vector-mediated gene transfer is also a suitable method for the introduction of a recombinant vector according to the invention into a cell. Appropriate viral vectors include adenovirus vectors and adeno-associated virus vectors, retrovirus vectors and herpesvirus vectors.

Adenovirus vectors can be used to introduce the gene according to the invention into a cell. Adenoviruses are linear, double stranded DNA viruses complexed with core proteins and surrounded by capsid proteins. The common serotypes 2 and 5, which are not associated with any human malignancies, are typically the base vectors. By deleting parts of the virus genome and inserting the desired gene under the control of a constitutive viral promoter, the virus becomes a replication deficient vector capable of transferring the exogenous DNA to differentiated, non-proliferating cells. To enter cells, the adenovirus fibre interacts with specific receptors on the cell surface, and the adenovirus surface proteins interact with the cell surface integrins. The virus penton-cell integrin interaction provides the signal that brings the exogenous gene-containing virus into a cytoplasmic endosome. The adenovirus breaks out of the endosome and moves to the nucleus, the viral capsid falls apart, and the exogenous DNA enters the cell nucleus where it functions, in an epichromosomal fashion, to express the exogenous gene. Detailed discussions of the use of adenoviral vectors for gene therapy can be found in Berkner, *Biotechniques* 6:616–629 (1988) and Trapnell, *Advanced Drug Delivery Rev.* 12:185–199 (1993), which are herein incorporated by reference. Adenovirus-derived vectors, particularly non-replicative adenovirus vectors, are characterized by their ability to accommodate exogenous DNA of 7.5 kB, relative stability, wide host range, low pathogenicity in man, and high titers ($10^4$ to $10^5$ plaque forming units per cell). See Stratford-Perricaudet et al., *PNAS* 89:2581 (1992).

Adeno-associated virus (AAV) vectors can be used also to introduce the gene according to the invention into a cell. AAV is a linear single-stranded DNA parvovirus that is endogenous to many mammalian species. AAV has a broad host range despite the limitation that AAV is a defective parvovirus which is dependent totally on either adenovirus or herpesvirus for its reproduction in vivo. The use of AAV as a vector for the introduction into target cells of exogenous DNA is well-known in the art. See, e.g., Lebkowski et al., *Mole. & Cell. Biol.* 8:3988 (1988), which is incorporated herein by reference. In these vectors, the capsid gene of AAV is replaced by a desired DNA fragment, and transcomplementation of the deleted capsid function is used to create a recombinant virus stock. Upon infection, the recombinant virus uncoats in the nucleus and integrates into the host genome.

Another suitable virus-based gene delivery mechanism is retroviral vector-mediated gene transfer. In general, retroviral vectors are well-known in the art. See Breakfield et al., *Mole. Neuro. Biol.* 1:339 (1987) and Shih et al., in *Vaccines* 85: 177 (Cold Spring Harbor Press 1985). A variety of retroviral vectors and retroviral vector-producing cell lines can be used to introduce DNA into cells. Appropriate retroviral vectors include Moloney Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus. These vectors include replication-competent and replication-defective retroviral vectors. In addition, amphotropic and xenotropic retroviral vectors can be used. In carrying out the invention, retroviral vectors can be introduced into a cell directly or in the form of free retroviral vector producing-cell lines. Suitable producer cells include fibroblasts, neurons, glial cells, keratinocytes, hepatocytes, connective tissue cells, ependymal cells, chromaffin cells. See Wolff et al., *PNAS* 84:3344 (1989).

Retroviral vectors generally are constructed such that the majority of its structural genes are deleted or replaced by exogenous DNA of interest, and such that the likelihood is reduced that viral proteins will be expressed. See Bender et al., *J. Virol.* 61:1639 (1987) and Armento et al., *J. Virol.* 61:1647 (1987), which are herein incorporated by reference. A retroviral vector employed in the present invention must integrate into the genome of the host cell genome, an event which occurs only in mitotically active cells. The necessity for host cell replication effectively limits retroviral gene expression to tumor cells, which are highly replicative, and to a few normal tissues. The normal tissue cells theoretically most likely to be transduced by a retroviral vector, therefore, are the endothelial cells that line the blood vessels that supply blood to the tumor. In addition, it is also possible that a retroviral vector would integrate into white blood cells both in the tumor or in the blood circulating through the tumor.

The spread of retroviral vector to normal tissues, however, is limited. The local administration to a tumor of a retroviral vector or retroviral vector producing cells will restrict vector propagation to the local region of the tumor, minimizing transduction, integration, expression and subsequent cytotoxic effect on surrounding cells that are mitotically active. Both replicatively deficient and replicatively competent retroviral vectors can be used in the invention, subject to their respective advantages and disadvantages. For instance, for tumors that have spread regionally, such as lung cancers, the direct injection of cell lines that produce replication-deficient vectors may not deliver the vector to a large enough area to completely eradicate the tumor, since the vector will be released only from the original producer cells and their progeny, and diffusion is limited. Similar constraints apply to the application of replication deficient vectors to tumors that grow slowly, such as human breast cancers which typically have doubling times of 30 days versus the 24 hours common among human gliomas. The much shortened survival-time of the producer cells, probably no more than 7–14 days in the absence of immunosuppression, limits to only a portion of their replicative cycle the exposure of the tumor cells to the retroviral vector. The use of replication-defective retroviruses for treating tumors requires producer cells and is limited because each replication-defective retrovirus particle can enter only a single cell and cannot productively infect others thereafter. Because these replication-defective retroviruses cannot spread to other tumor cells, they would be unable to completely penetrate a deep, multilayered tumor in vivo. See Markert et al., *Neurosurg.* 77: 590 (1992). The injection of replication-competent retroviral vector particles or a cell line that produces a replication-competent retroviral vector virus may prove to be a more effective therapeutic because a replication competent retroviral vector will establish a productive infection that will transduce cells as long as it persists. Moreover, replicatively competent retroviral vectors may follow the tumor as it metastasizes, carried along and propagated by transduced tumor cells. The risks for complications are greater, with replicatively competent vectors, however. Such vectors may pose a greater risk then replicatively deficient vectors of transducing normal tissues, for instance. The risks of undesired vector propagation for each type of cancer and affected body area can be weighed against the advantages in the situation of replicatively competent verses replicatively deficient retroviral vector to determine an optimum treatment.

Both amphotropic and xenotropic retroviral vectors may be used in the invention. Amphotropic virus have a very broad host range that includes most or all mammalian cells, as is well known to the art. Xenotropic viruses can infect all mammalian cell cells except mouse cells. Thus, amphotropic and xenotropic retroviruses from many species, including cows, sheep, pigs, dogs, cats, rats, and mice, inter alia can be used to provide retroviral vectors in accordance with the invention, provided the vectors can transfer genes into proliferating human cells in vivo.

Clinical trials employing retroviral vector therapy treatment of cancer have been approved in the United States. See Culver, *Clin. Chem.* 40: 510 (1994). Retroviral vector-containing cells have been implanted into brain tumors growing in human patients. See Oldfield et al., *Hum. Gene Ther.* 4: 39 (1993). These retroviral vectors carried the HSV-1 thymidine kinase (HSV-tk) gene into the surrounding brain tumor cells, which conferred sensitivity of the tumor cells to the antiviral drug ganciclovir. Some of the limitations of current retroviral based cancer therapy, as described by Oldfield are: (1) the low titer of virus produced, (2) virus spread is limited to the region surrounding the producer cell implant, (3) possible immune response to the producer cell line, (4) possible insertional mutagenesis and transformation of retroviral infected cells, (5) only a single treatment regimen of pro-drug, ganciclovir, is possible because the "suicide" product kills retrovirally infected cells and producer cells and (6) the bystander effect is limited to cells in direct contact with retrovirally transformed cells. See Bi et al., *Human Gene Therapy* 4: 725 (1993).

Yet another suitable virus-based gene delivery mechanism is herpesvirus vector-mediated gene transfer. While much less is known about the use of herpesvirus vectors, replication-competent HSV-1 viral vectors have been described in the context of antitumor therapy. See Martuza et al., *Science* 252: 854 (1991), which is incorporated herein by reference.

The present invention also contemplates pharmaceutical compositions comprising the above described vectors.

It is expected that one skilled in the art having the benefit of the foregoing disclosure and the references cited therein would recognize the relative strengths and weaknesses of each gene delivery system in determining an appropriate method for the introduction of a recombinant vector containing the polynucleotide according to the invention into a cell.

Apart from the therapy of diseases such as cancers or Alzheimer's disease, it is consequently very important to be able to have the system allowing the detection of the diseases in question as early as possible.

The present invention thus likewise relates to a diagnostic agent for the determination and the monitoring of cancers and/or of Alzheimer's disease, comprising a sequence according to the invention to be used as a nucleotide probe or as an amplification primer.

The present invention thus likewise relates to a diagnostic agent for the determination and the monitoring of cancers and/or of Alzheimer's disease, comprising at least one antibody, preferably monoclonal, against the peptide sequence defined above as being the product of expression of a sequence according to the invention. Thus, in one embodiment, the present invention is directed to a method of detecting the presence of the presenilin 1 gene in a mammalian tissue sample, said method comprising the steps of:

(a) contacting said tissue sample with the polynucleotide molecule of the present invention under conditions of hybridization, and (b) detecting the formation of a hybrid of said molecule with the presenilin 1 gene. The molecule of the invention includes cDNA of the presenilin 1 gene, an anti-sense sequence thereof or cDNA of TSIP2. Suitable hybridization conditions and detection techniques are set forth in Sambrook et al. *Molecular Cloning: a laboratory manual* (1989) and are well known to the skilled artisan.

The invention is not limited to the description above and will be better understood in the light of the example below which, however, is not given other than by way of illustration.

EXAMPLES

Example 1

Cloning of the total length of the cDNA of TSIP2

The cDNA of TSIP2 (90 bp) isolated by differential analysis of the mRNAs was then extended to the total coding region of this gene by RACE-PCR (rapid amplification of the ends of cDNA). The total length of the cDNA of TSIP2 was amplified by means of the Marathon cDNA amplification kit (Clontech Laboratories), according to the instructions of the manufacturer. The anti-sense primer used to amplify 2.7 kb of the 5' segment of the transcript is the following: 5'CACCAGCCACTCATCGCTTTAAT3' (SEQ ID NO:3). The amplified product was cloned by means of the TA cloning system (Invitrogène), according to the instructions of the manufacturer.

Northern blot analysis

Northern blots were carried out using 2 μg of polyA$^+$ RNA as described previously (Sambrook et al. *Molecular Cloning: a laboratory manual* (1989)). The total cDNA of TSIP2 (2.8 kb) was used as a probe. The Northern blots were hybridized with probes labelled with $P^{32}$ primed at random.

Cells

M1-LTR6 cells stably transfected with a val 135 p53 mutant which is sensitive to temperature, K562/KS cells and U937/US cells have been described previously. For the p21 Waf1 transfectants of the U937 cells, the total cDNA coding for the human p21$^{WAF-1}$ gene was cloned in the EcoR1 site of the phagemid vector pBK-RSV (Stratagène). After selection, these cells express p21 protein at a high level and have a strongly suppressed malignant phenotype.

Transfections of PS1

The total cDNA of TSIP2 (2.8 kb) was cloned in the EcoR1 site of the pBK-RSV vector (Stratagène). The U937 cells (3×10$^6$) were transfected with 20 μg of DNA/30 μg of Lipofectin (Gibco BRL). The stable transfectants, containing the anti-sense cDNA of TSIP2, were obtained after three weeks of selection with 1.5 mg/ml of G418 (SIGMA).

Western blot analysis

The protein extraction and the employment of samples for detection with an anti-C-terminal end polyclonal antibody were carried out under standard conditions: heating of the samples to 95° C. for 5 minutes, followed by direct cooling on ice. Alternatively, for detection with anti-N-terminal end monoclonal antibodies, the proteins are extracted by the addition of NP 40 to 1% and of Triton X-100 to 1%, followed by the addition of an SDS sample buffer with a final urea concentration of 8M, heated for 20 minutes at 56° C. and directly loaded on the gel. The Western blots were carried out with 10 µg of proteins. The blots were hybridized all night at 4° C. with a goat S182 polyclonal antibody directed against the C-terminal fragment of S182 (C-20, Santa Cruz Laboratories). This is an affinity-purified goat polyclonal antibody directed against a peptide corresponding to the amino acids 449 to 468. The signals were detected using a secondary antibody (anti-goat, coupled to peroxidase). Alternatively, the Western blots were hybridized all night at 4° C. with an anti-presenilin 1 monoclonal antibody (MAB1563, Chemicon International Inc.). This antibody is directed against a fusion protein antigen containing the N-terminal end of human PS1 (residues 21 to 80). The signals were detected by a secondary antibody (anti-rat, coupled to peroxidase).

Analysis of tumorigenicity

Injection into scid/scid mice was carried out as described previously (Telerman, A. et al. A model for tumoral suppression using H-1 parvovirus. *Proc. Natl. Acad. Sci.* USA 90, 8702–8706 (1993)). $10^7$ cells were injected per site. The animals were monitored for three months. The Mann-Whitney test was used for statistical analysis.

Flow cytometry

In the cases of the determination of the content of propidium iodide in the DNA and of the TUNEL test, the cells were washed with PBS containing 5% of BSA. The cell aggregates were resuspended in 250 µl of PBS and then in 250 µl of PBS containing 4% of paraformaldehyde. After an incubation period of 15 minutes at 4° C., the cells were washed and suspended in 5 ml of ice-cold 70% ethanol and stored all night at –20° C. The propidium iodide was added to the cell suspension at a final concentration of 15 µg/µl and the cells were analysed in a cell sorter. The TUNEL test (Boehringer) was employed according to the information of the manufacturer and the cells were analysed in a cell sorter.

Growth curve $10^4$ cells were resuspended in RPMI-10% FCS and counted every two days.

PCR analysis

To detect the integration of the cDNA construct of PS1 into the genomic DNA, samples were analysed with a series of primers superimposing on the plasmid and on the whole of the coding region of the PS1 cDNA.

Example 2

Presenilin 1 is Antiapoptotic

Figure 5B:
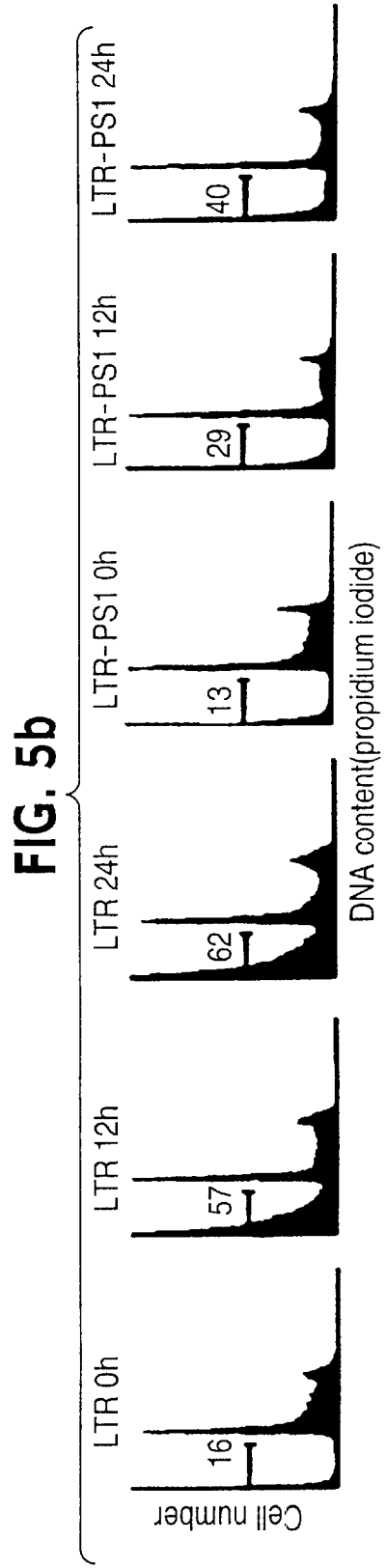
FIG. 5b shows a FACS analysis of the DNA content in LTR-5 cells and PS1 transfectants (LTR-PS1) at 37 degrees centigrade after 12 hours and 24 hours of incubation at 32 degrees centigrade.
Figure 5C:
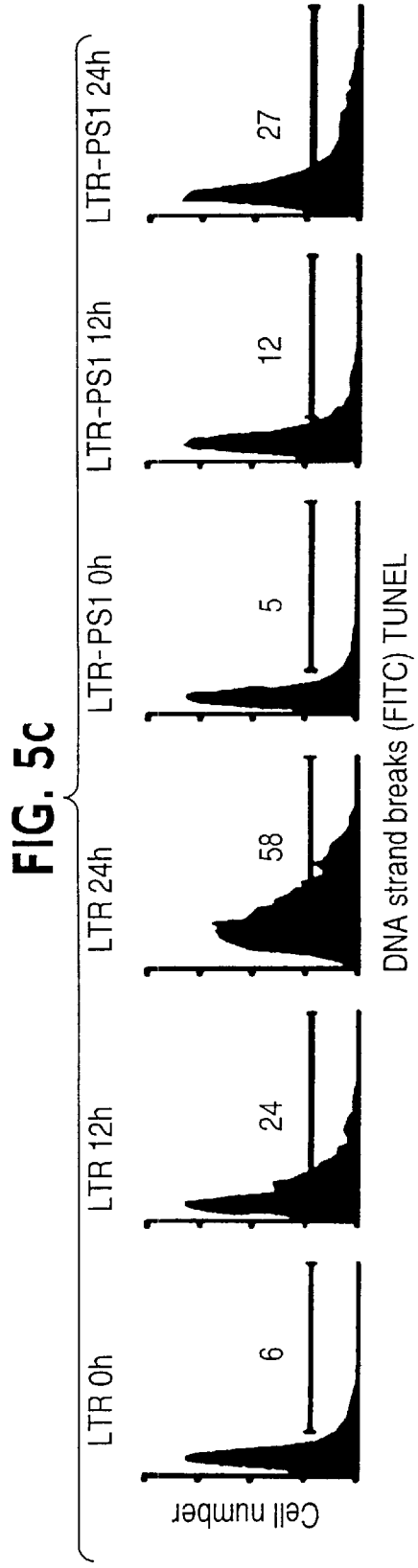
FIG. 5c shows the results of a TUNEL assay of the DNA content in LTR-6 cells and PS1 transfectants (LTR-PS1) at 37 degrees centigrade after 12 hours and 24 hours of incubation at 32 degrees centigrade.

PS1 expression is repressed under conditions of p53-mediated apoptosis; moreover its inhibition by anti-sense RNA is correlated with the induction of apoptosis. These observations gave rise to the proposal that PS1 may possess an antiapoptotic function. To investigate this notion, PS1's ability to protect cells against the apoptotic action of p53 was tested. The experimental system chosen for this purpose consisted of LTR6 cells. These cells are derived from the murine myeloid leukemia cell line M1, through stable transfection with the temperature sensitive p53 mutant p53val135. Upon shift from 37 degrees centegrade to 32 degrees centegrade, p53val135 regains wild type p53 function. This, in turn, results in apoptotic cell death. Of particular note, LTR6 cells exhibit a pronounced down regulation of PS1 expression following wild type p53 activation. Transfection of LTR6 cells with a PS1 expression vector resulted in elevated PS1 expression (FIG. 5a) even after induction of wild type p53. This was true for both the 50 kDa PS1 full length protein and the 30 kDa N-terminal fragment of PS1. Importantly, induction of p53-mediated apoptosis at 32 degrees centigrade was markedly suppressed in cells that were allowed to maintain relatively high PS1 levels after p53 activation (FIGS. 5b and 5c). This suppression was apparent irrespective of whether apoptosis was measured by accumulation of cells with sub-G1 DNA content (FIG. 5b) or by the TUNEL assay (FIG. 5C) levels.

Antibodies and Western blot Analysis: Polyclonal anti-PS1 antibodies (95/23) against the N-terminal fragment were previously described. Proteins were extracted adding 1% NP 40 and 1% Triton X-100, followed by the addition of SDS sample buffer with a final concentration of 8 M urea, heated for 20 minutes at 56 degrees cetnigrade and directly loaded on the gel (10 µg of protein). Signals were detected using a secondary antibody coupled to peroxidase.

Cells and PS1 transfectants: LTR6 cells stably transfected with the temperature sensitive p53Val135 mutant have been previously described. LTR6 cells were transfected, using Lipofectin (Life Technologies) with the full length mouse PS1 cDNA subcloned in pcDNA3.1/Zeo (Invitrogen). Selection was performed using Zeocin (50 µg/ml) for 6 weeks.

Flow cytometry. For both the propidium iodide DNA content profile and TUNEL assay, cells were processed as described above.

All references set forth above are herein incorporated by reference.

What is claimed is:

1. A composition for inhibiting growth of tumor cells, comprising an effective inhibiting amount of an antisense polynucleotide 10–50 nucleobases in length targeted to a nucleic acid molecule encoding presenilin-1, wherein said antisense polynucleotide specifically hybridizes with and inhibits the expression of presenilin-1, and wherein said antisense polynucleotide comprises SEQ ID NO: 3, wherein inhibition of presenilin-1 expression results in reduction of tumor cell growth.

2. The composition of claim 1, wherein said antisense polynucleotide is a cDNA molecule.

3. The composition of claim 1, wherein said antisense polynucleotide is encapsulated in a liposome.

4. The composition of claim 1, wherein said composition further comprises a pharmaceutically acceptable carrier.

5. The composition of claim 1, wherein said polynucleotide further comprises a cellular targeting sequence.

6. The composition of claim 1, wherein said polynucleotide is linked to a polyamine.

7. The composition of claim 1, wherein said polynucleotide is about 20 to 30 nucleotides in length.

8. The composition of claim 1, wherein said polynucleotide is about 14 to 25 nucleotides in length.

9. The composition of claim 1, wherein said polynucleotide is about 10 to 15 nucleotides in length.

10. A method of reducing tumor cell growth, comprising introducing an effective inhibiting amount of a polynucleotide, which is antisense to all or part of the presenilin 1 gene set forth as SEQ ID NO:2, into tumor cells ex vivo and implanting cells containing said polynucleotide into a subject wherein cellular expression of the presenilin 1 gene is inhibited and whereby tumor reduction is obtained.

11. The method of claim 10, wherein the antisense polynucleotide has a sequence of SEQ ID NO: 3.

12. The method of claims 10 or 11, wherein said polynucleotide is about 20 to 30 nucleotides in length.

13. The method of claims 10 or 11, wherein said polynucleotide is about 14 to 25 nucleotides in length.

14. The method of claims 10 or 11, wherein said polynucleotide is about 10 to 15 nucleotides in length.

15. The method of claim 10, wherein the antisense polynucleotide is a cDNA molecule.

16. The method of claim 10, wherein the antisense polynucleotide is encapsulated in a liposome.

\* \* \* \* \*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 716 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

| | | | | | | |
|---|---|---|---|---|---|---|
| TAGCTTTGAC | CGTGGGCATG | GAGATTTACC | CGCACTGTGA | ACTCTCTAAG | GTAAACAAAG | 60 |
| TCAGGTGACC | AAACAGAGCT | GCCATCTTCC | ACACCATGTT | GGAAATAAAA | CCGTCCTAGC | 120 |
| TGGAACCCTT | ACTGTCCCAG | GAGGTTCCGT | GTGGGGTGG | CACTGGGCCG | GGCCTCCCTC | 180 |
| TCAGGCTCCT | TTGCTGCCCA | CTTGTAGTTT | AAATAAGGAC | ACCGCCCTAC | ACAAACCTCA | 240 |
| CCCCTGTCAC | ATCCAGTGAC | TCTGACCACT | TTAGTTCTCA | AACTCTCTCA | CTATTATCTG | 300 |
| TGGTTGCCGT | TTCTTCCCAA | GGCCAGCCTG | GACGAATTTG | GGGTTGCTCT | ATCCTGAGAG | 360 |
| TTGTAACCTC | AACTTCCAAA | GTTTATATTT | TCTTGAAATG | ATGGATCTAT | TGCTCAACAG | 420 |
| TCCCTGTCAT | CCTTAAGTGA | CTTCTGGGTT | TCCCACAAAT | TCCTCACTTT | TAGACACACT | 480 |
| CTAAGCTTAC | TTCTGGCCTG | GATGCTTCCT | CTCCCTGTCT | CTCCCTTGCC | CCACAGCGGT | 540 |
| TCCCTGACAG | CAGACAAGGC | AGCTCTGGGA | GGTAGCTAGT | ATCCAATAAC | CCAGGGGTTT | 600 |
| CCTCATGTGA | TGCAAATACT | ACGTGTCAAC | CAATCAGTGC | TGTCAACGGG | CTGCCATAGC | 660 |
| TCCTTCGATG | GCAAATAGGA | TGTGTGCCCA | AAGAATAAAG | CGATCAGTGG | CTGGTG | 716 |

(2) INFORMATION FOR SEQ ID NO:2:

(i) SEQUENCE CHARACTERISTICS:
        (A) LENGTH: 2680 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

| | | | | | | |
|---|---|---|---|---|---|---|
| CACCGGTGAG | ACCTCTAGGG | CGGGGCCTAG | GACGACCTGC | TCCGTGGGCC | GCGAGTATTC | 60 |
| GTCGGAAACA | AAACAGCGGC | AGCTGAGGCG | GAAACCTAGG | CTGCGAGCCG | GCCGCCCGGG | 120 |
| CGCGGAGAGA | GAAGGAACCA | ACACAAGACA | GCAGCCCTTC | GAGGTCTTTA | GGCAGCTTGG | 180 |
| AGGAGAACAC | ATGAGAGAAA | GAATCCCAAG | AGGTTTTGTT | TTCTTTGAGA | AGGTATTTCT | 240 |
| GTCCAGCTGC | TCCAATGACA | GAGATACCTG | CACCTTTGTC | CTACTTCCAG | AATGCCCAGA | 300 |
| TGTCTGAGGA | CAGCCACTCC | AGCAGCGCCA | TCCGGAGCCA | GAATGACAGC | CAAGAACGGC | 360 |
| AGCAGCAGCA | TGACAGGCAG | AGACTTGACA | ACCCTGAGCC | AATATCTAAT | GGGCGGCCCC | 420 |
| AGAGTAACTC | AAGACAGGTG | GTGGAACAAG | ATGAGGAGGA | AGACGAAGAG | CTGACATTGA | 480 |
| AATATGGAGC | CAAGCATGTC | ATCATGCTCT | TTGTCCCCGT | GACCCTCTGC | ATGGTCGTCG | 540 |
| TCGTGGCCAC | CATCAAATCA | GTCAGCTTCT | ATACCCGGAA | GGACGGTCAG | CTAATCTACA | 600 |
| CCCCATTCAC | AGAAGACACT | GAGACTGTAG | GCCAAAGAGC | CCTGCACTCG | ATCCTGAATG | 660 |
| CGGCCATCAT | GATCAGTGTC | ATTGTCATTA | TGACCATCCT | CCTGGTGGTC | CTGTATAAAT | 720 |
| ACAGGTGCTA | CAAGGTCATC | CACGCCTGGC | TTATTATTTC | ATCTCTGTTG | TTGCTGTTCT | 780 |
| TTTTTTCGTT | CATTTACTTA | GGGGAAGTAT | TTAAGACCTA | CAATGTCGCC | GTGGACTACG | 840 |
| TTACAGTAGC | ACTCCTAATC | TGGAATTTTG | GTGTGGTCGG | GATGATTGCC | ATCCACTGGA | 900 |
| AAGGCCCCCT | TCGACTGCAG | CAGGCGTATC | TCATTATGAT | CAGTGCCCTC | ATGGCCCTGG | 960 |
| TATTTATCAA | GTACCTCCCC | GAATGGACCG | CATGGCTCAT | CTTGGCTGTG | ATTTCAGTAT | 1020 |
| ATGATTTGGT | GGCTGTTTTA | TGTCCCAAAG | GCCCACTTCG | TATGCTGGTT | GAAACAGCTC | 1080 |
| AGGAAAGAAA | TGAGACTCTC | TTTCCAGCTC | TTATCTATTC | CTCAACAATG | GTGTGGTTGG | 1140 |

```
                                                        -continued

TGAATATGGC TGAAGGAGAC CCAGAAGCCC AAAGGAGGGT ACCCAAGAAC CCCAAGTATA    1200

ACACACAAAG AGCGGAGAGA GAGACACAGG ACAGTGGTTC TGGGAACGAT GATGGTGGCT    1260

TCAGTGAGGA GTGGGAGGCC CAAAGAGACA GTCACCTGGG GCCTCATCGC TCCACTCCCG    1320

AGTCAAGAGC TGCTGTCCAG GAACTTTCTG GGAGCATTCT AACGAGTGAA GACCCGGAGG    1380

AAAGAGGAGT AAAACTTGGA CTGGGAGATT TCATTTTCTA CAGTGTTCTG GTTGGTAAGG    1440

CCTCAGCAAC CGCCAGTGGA GACTGGAACA CAACCATAGC CTGCTTTGTA GCCATACTGA    1500

TCGGCCTGTG CCTTACATTA CTCCTGCTCG CCATTTTCAA GAAAGCGTTG CCAGCCCTCC    1560

CCATCTCCAT CACCTTCGGG CTCGTGTTCT ACTTCGCCAC GGATTACCTT GTGCAGCCCT    1620

TCATGGACCA ACTTGCATTC CATCAGTTTT ATATCTAGCC TTTCTGCAGT TAGAACATGG    1680

ATGTTTCTTC TTTGATTATC AAAAACACAA AAACAGAGAG CAAGCCCGAG GAGGAGACTG    1740

GTGACTTTCC TGTGTCCTCA GCTAACAAAG GCAGGACTCC AGCTGGACTT CTGCAGCTTC    1800

CTTCCGAGTC TCCCTAGCCA CCCGCACTAC TGGACTGTGG AAGGAAGCGT CTACAGAGGA    1860

ACGGTTTCCA ACATCCATCG CTGCAGCAGA CGGTGTCCCT CAGTGACTTG AGAGACAAGG    1920

ACAAGGAAAT GTGCTGGGCC AAGGAGCTGC CGTGCTCTGC TAGCTTTGAC CGTGGGCATG    1980

GAGATTTACC CGCACTGTGA ACTCTCTAAG GTAAACAAAG TGAGGTGAAC CAAACAGAGC    2040

TGCCATCTTC CACACCATGT TGGAAATAAA ACCGTCCTAG CTGGAACCCT TACTGTCCCA    2100

GGAGGTTCCG TGTGGGGGTG GCACTGGGCC GGGCCTCCCT CTCAGGCTCC TTTGCTGCCC    2160

ACTTGTAAGT TTAAATAAGG ACACCGCCCT ACACAAACCT CACCCCTGTC ACATCCAGTG    2220

ACTCTGACCA CTTTAGTTCT CAAACTCTCT CACTATTATC TGTGGTTGCC GTTTCTTCCC    2280

AAGGCCAGCC TGGACGAATT TGGGGTTGCT CTATCCTGAG AGTTGTAACC TCAACTTCCA    2340

AAGTTTATAT TTTCTTGAAA TGATGGATCT ATTGCTCAAC AGTCCCTGTC ATCCTTAAGT    2400

GACTTCTGGG TTTCCCACAA ATTCCTCACT TTTAGACACA CTCTAAGCTT ACTTCTGGCC    2460

TGGATGCTTC CTCTCCCTGT CTCTCCCTTG CCCCACAGCG GTTCCCTGAC AGCAGACAAG    2520

GCAGCTCTGG GAGGTAGCTA GTATCCAATA ACCCAGGGGT TTCCTCATGT GATGCAAATA    2580

CTACGTGTCC AACCAATCAG TGCTGTCAAC GGGCTGCCAT AGCTCCTTCG ATGGCAAATA    2640

GGATGTGTGC CCAAAGAATT AAAGCGATCA GTGGCTGGTG                         2680

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:3:

CACCAGCCAC TCATCGCTTT AAT                                             23
```